United States Patent
Hao et al.

(10) Patent No.: US 11,744,627 B2
(45) Date of Patent: Sep. 5, 2023

(54) INTEGRATED TARGETED KYPHOPLASTY SYSTEM

(71) Applicant: HAO, Ding-jun, Xi'an (CN)

(72) Inventors: Ding-jun Hao, Xi'an (CN); Biao Wang, Xi'an (CN)

(73) Assignee: Hao Ding-jun, Xi'an (CN)

( * ) Notice: Subject to any disclaimer, the term of this patent is extended or adjusted under 35 U.S.C. 154(b) by 73 days.

(21) Appl. No.: 17/042,120

(22) PCT Filed: Sep. 17, 2019

(86) PCT No.: PCT/CN2019/106268
§ 371 (c)(1),
(2) Date: Sep. 26, 2020

(87) PCT Pub. No.: WO2021/031267
PCT Pub. Date: Feb. 25, 2021

(65) Prior Publication Data
US 2023/0097258 A1    Mar. 30, 2023

(30) Foreign Application Priority Data
Aug. 16, 2019 (CN) .......................... 201910760702.2

(51) Int. Cl.
*A61B 17/88* (2006.01)
*A61B 17/34* (2006.01)

(52) U.S. Cl.
CPC ...... *A61B 17/8811* (2013.01); *A61B 17/3472* (2013.01); *A61B 17/8816* (2013.01);
(Continued)

(58) Field of Classification Search
CPC . A61B 17/88; A61B 17/8802; A61B 17/8805; A61B 17/8811; A61B 17/8816;
(Continued)

(56) References Cited

U.S. PATENT DOCUMENTS 10,398,485 B2 *   9/2019  Kallmes ............. A61B 17/8858
11,229,466 B2 *   1/2022  Kallmes ............. A61B 17/8816
(Continued)

FOREIGN PATENT DOCUMENTS

CN    101404946 A        4/2009
CN    103690228 A    *   4/2014    ......... A61B 17/1642
(Continued)

OTHER PUBLICATIONS

International Search Report (PCT/CN2019/106268); dated Apr. 15, 2020.

*Primary Examiner* — Eric S Gibson
(74) *Attorney, Agent, or Firm* — W&G Law Group

(57) ABSTRACT

An integrated targeted kyphoplasty system includes a piercing head, a tube body and a tube body handle. The tube body has an end connected to the piercing head and is provided with a balloon and a guider at an end of the balloon, and another end connected to the tube body handle and provided with a guide knob for controlling the guider to be bent and a pressure pump connector communicating the balloon. The piercing head is provided with a cement outlet, a cement channel is in center of the tube body, and the tube body handle is provided with a cement inlet. The cement outlet, cement channel and cement inlet communicate with each other. The device requires for only one piercing to complete entire KP surgical treatment without changing any tools, greatly decreasing radiation exposure rate of the patient during operation and the pain caused by multiple operations.

8 Claims, 2 Drawing Sheets

(52) U.S. Cl.
CPC ...... *A61B 17/8819* (2013.01); *A61B 17/8855* (2013.01); *A61B 17/8858* (2013.01)

(58) Field of Classification Search
CPC ............ A61B 17/8819; A61B 17/8822; A61B 17/8825; A61B 17/885; A61B 17/8852; A61B 17/8855; A61B 17/8858
See application file for complete search history.

(56) References Cited

U.S. PATENT DOCUMENTS

| | | | |
|---|---|---|---|
| 2009/0299282 A1* | 12/2009 | Lau | A61M 29/02 604/99.01 |
| 2011/0282348 A1 | 11/2011 | Shin | |
| 2012/0143202 A1 | 6/2012 | Linderman | |
| 2016/0310193 A1* | 10/2016 | Lv | A61B 17/1642 |
| 2018/0199971 A1* | 7/2018 | Kallmes | A61B 17/8858 |
| 2019/0365445 A1* | 12/2019 | Kallmes | A61B 17/8816 |
| 2023/0097258 A1* | 3/2023 | Hao | A61B 17/3472 606/94 |

FOREIGN PATENT DOCUMENTS

| | | | | |
|---|---|---|---|---|
| CN | 104718001 A | | 6/2015 | |
| CN | 103690228 B | * | 11/2015 | ......... A61B 17/1642 |
| CN | 208511688 U | | 2/2019 | |
| CN | 110327107 A | * | 10/2019 | ......... A61B 17/3421 |
| EP | E P-3081252 A1 | * | 10/2016 | ......... A61B 17/1642 |
| EP | 3081252 B1 | * | 8/2018 | ......... A61B 17/1642 |
| JP | 2009285135 A | | 12/2009 | |
| JP | 2016535660 A | * | 11/2016 | |
| JP | 6311031 B2 | * | 4/2018 | ........ A61M 25/0082 |
| JP | 2021053462 A | * | 4/2021 | ......... A61B 17/8802 |
| WO | WO-2009051897 A1 | * | 4/2009 | ......... A61B 17/1757 |
| WO | WO-2015085837 A1 | * | 6/2015 | ......... A61B 17/1642 |
| WO | WO-2021031267 A1 | * | 2/2021 | ......... A61B 17/3421 |

* cited by examiner

INTEGRATED TARGETED KYPHOPLASTY SYSTEM

TECHNICAL FIELD

The present disclosure relates to the field of medical devices, and in particular, to an integrated targeted kyphoplasty system.

BACKGROUND

Osteoporosis is the most common bone metabolic disease in the world, and the disease is very common with acceleration of aging. The most common result of spinal osteoporosis is a vertebral compression fracture. With aging of the entire population, an incidence of osteoporotic vertebral compression fracture (OVCF) is alarmingly high. According to statistics, an incidence of OVCF is as high as 50% among women aged over 80, and as high as 25% among women aged 70 to 79. For about one-third of them, conservative treatments are ineffective, and patients with severe pain usually require minimally invasive vertebroplasty or kyphoplasty for treatment, both of which have achieved very good therapeutic effects in clinic. Among them, kyphoplasty (KP) is a new technology that uses balloon reduction in combination with the vertebroplasty. Compared with the vertebroplasty, the kyphoplasty has advantages of a low risk of leakage of bone cement, better recovery of vertebral body height, and better improvement of spinal curvature, so that the kyphoplasty is more widely used in clinical practice.

KP can use bilateral pedicle approach or unilateral pedicle approach during specific surgical operations. The unilateral approach decreases half of surgical time and surgical trauma of the bilateral approach, and clinical efficacy is superior to that of the bilateral approach. However, currently, using clinical unilateral approach to carry out KP has following deficiencies: ①. due to limitations of current operating tools, and influences of surgical techniques, timing of bone cement injection, etc., when bone cement distribution is poor in unilateral surgical operation for some patients, it often needs to make a change and use the bilateral surgical approach instead; ②. a flow direction of the bone cement in the vertebral body is uncontrollable, so targeted injection of the bone cement cannot be accurately achieved, and due to the uncontrollability of the bone cement flow, although leakage of bone cement is less than that in the case of the vertebroplasty, it still occurs from time to time; ③. surgical operation tools are relatively cumbersome, an operation channel needs to be replaced after piercing using a piercing needle is completed, a balloon should be placed after the operation channel is well arranged, and after the balloon is reset, it is required to remove the balloon and install the bone cement injection device, as a result, such repeated operations increase a number of times of X-ray exposure of the patient, moreover, since the KP is often carried out under local anesthesia, replacing the tools for many times make the patient suffer increased number of times of pain and have relatively poor experience during the surgery.

SUMMARY

In order to avoid the above-mentioned shortcomings and deficiencies of the current KP, the present disclosure provides an integrated targeted kyphoplasty system, and this device requires for only one piercing to complete an entire KP surgical treatment without changing any tools, which greatly decreases a radiation exposure rate of the patient during the operation and the pain caused by multiple operations.

To achieve the above objectives, the present disclosure adopts following technical solutions.

The present disclosure provides an integrated targeted kyphoplasty system, including a piercing head, a tube body, and a tube body handle.

The tube body has an end connected to the piercing head and provided with a guider at an end of the balloon.

The tube body has another end connected to the tube body handle and provided with a guide knob for controlling the guider to be bent and a pressure pump connector in communication with the balloon.

The piercing head is provided with a cement outlet, a cement channel is provided in a center of the tube body, the tube body handle is provided with a cement inlet, and the cement outlet, the cement channel and the cement inlet are in communication with each other.

The cement outlet is provided at a side of the piercing head.

An annular groove is provided at the end of the tube body, and the balloon is disposed in the annular groove.

The tube body is provided with an annular medium channel along an axial direction, and the medium channel communicates the balloon with the pressure pump connector.

The tube body is further provided with a pressure sensor, the pressure pump connector is provided at a side of the pressure sensor, and the medium channel is in communication with both the pressure sensor and the pressure pump connector.

The guider includes a soft spring disposed inside the tube body and a plurality of arc-shaped grooves distributed at an outer wall of the tube body. The tube body is provided with a traction rope disposed along an axial direction, and the soft spring is connected to the guide knob through the traction rope.

Two traction ropes are provided symmetrically, and the two traction ropes are connected to two direction control ends of the guide knob.

A push rod is further included, the push rod includes a thin rod and a push rod handle connected to the thin rod, and the thin rod can be inserted into the cement channel.

Compared with the related art, the present disclosure has following beneficial technical effects.

The integrated target kyphoplasty system of the present disclosure comes with an injection direction guider, an injection site of the bone cement can be changed to a targeted position desired by a surgeon within the vertebral body, so that the targeted injection of the bone cement in a fracture site can be achieved, and a leakage rate of the bone cement is decreased. Since the injection site of the bone cement can be changed to the targeted position desired by the surgeon within the vertebral body, the surgeon can place the injection site of the bone cement at an opposite side of the piercing to inject the bone cement, thereby making it easy to complete bilateral distribution of the bone cement and avoiding necessity of the bilateral approach. The targeted kyphoplasty system is an integrated design, and cost is lower than that of current surgical instruments, so it has better medical and economic values in the clinic.

Figure 1:
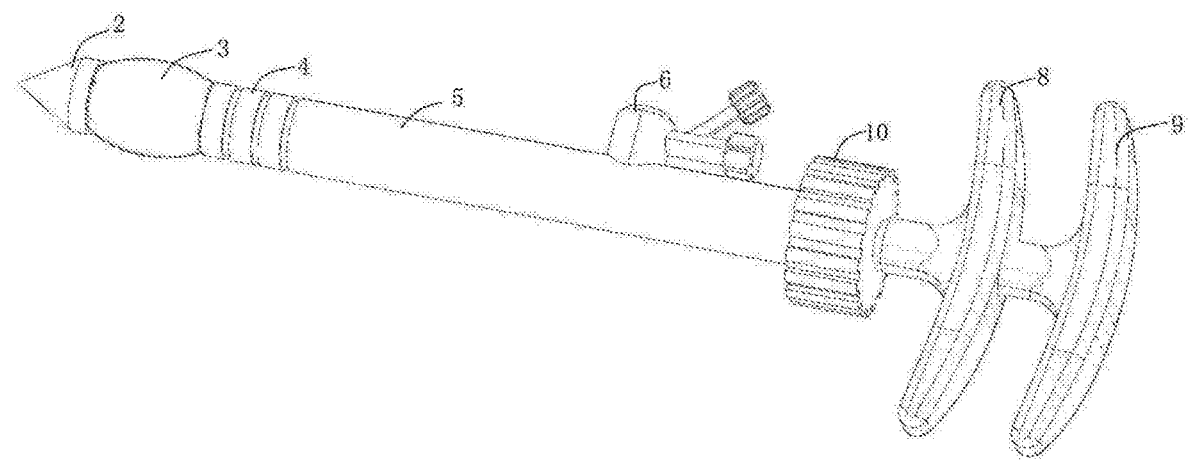
FIG. 1 is a perspective view of an integrated targeted kyphoplasty system of the present disclosure.
Figure 2:
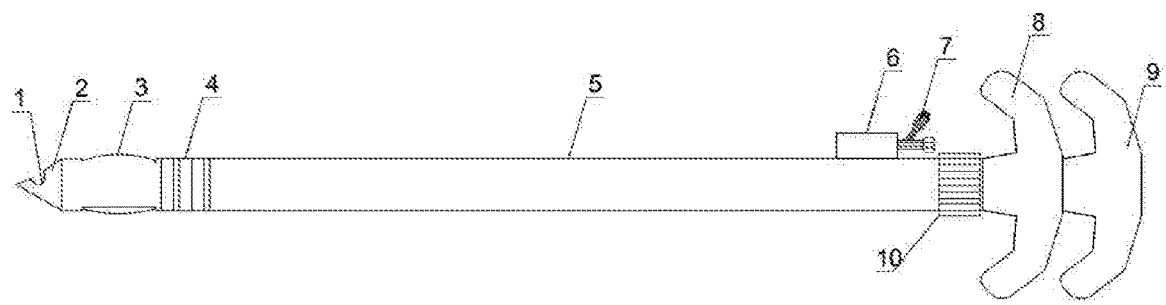
FIG. 2 is a front view of an integrated targeted kyphoplasty system of the present disclosure.
Figure 3:
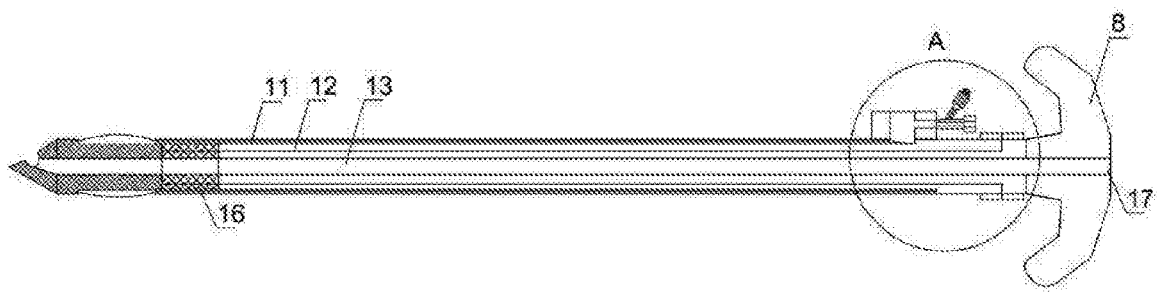
FIG. 3 is a partial cross-sectional view of FIG. 2.

In the figures, 1 is a cement outlet; 2 is a piercing head; 3 is a balloon; 4 is a guider; 5 is a tube body; 6 is a pressure sensor; 7 is a pressure pump connector; 8 is a tube body handle; 9 is a push rod; 10 is a guide knob; 11 is a medium channel; 12 is a traction rope; 13 is a cement channel; 14 is a thin rod; 15 is a push rod handle; 16 is a soft spring; 17 is a cement inlet.

DESCRIPTION OF EMBODIMENTS

In order to better illustrate the technical solutions in the embodiments of the present disclosure, the accompanying drawings required for illustrating the embodiments will be briefly introduced in the following. It should be noted that the accompanying drawings in the following are merely some embodiments of the present disclosure, and other accompanying drawings can be obtained based on these accompanying drawings for those skilled in the art without paying any creative labor.

In order to better illustrate the purpose, technical solutions and advantages of the present disclosure, specific implementation of the present disclosure will be further described in the following with reference to the accompanying drawings and embodiments, and the description is explanation of the present disclosure rather than limitation.

As shown in FIG. 1 to FIG. 6, the present disclosure provides an integrated targeted kyphoplasty system, including a piercing head 2, a tube body 5, and a tube body handle 8.

An end of the tube body 5 is connected to the piercing head 2, and the end of the tube body 5 connected to the piercing head 2 is provided with a balloon 3. The tube body 5 is provided with a guider 4 at an end of the balloon 3. The guider 4 can be bent in two directions, and a bending angle thereof ranges from 0 to 90°.

The other end of the tube body 5 is connected to the tube body handle 8, and the end of the tube body 5 connected to the tube body handle 8 is provided with a guide knob 10 for controlling the guider 4 to be bent and a pressure pump connector 7 in communication with the balloon 3. Both clockwise or counterclockwise rotation of the guide knob 10 can control the guider 4 to be bent, thereby making the piercing head 2 and the balloon 3 to change a direction. The pressure pump connector 7 is used to be connected to a balloon injector.

The piercing head 2 is provided with a cement outlet 1, and a cement channel 13 is provided in a center of the tube body 5. The tube body handle 8 is provided with a cement inlet 17. The cement outlet 1, the cement channel 13 and the cement inlet 17 are in communication with each other. The cement inlet 17 is used to be connected to a bone cement injector. Bone cement is rapidly injected via the cement channel 13, which can target positioning of the bone cement in the vertebral body.

The cement outlet 1 is provided at one side of the piercing head 2, and unilateral cement injection can be achieved.

An annular groove is provided at an end of the tube body 5, and the balloon 3 is disposed in the annular groove. When the balloon 3 is inflated, it expands outwards according to an outer contour of the annular groove, so as to effectively expand and reset a fracture site of the vertebral body.

The tube body 5 is provided with an annular medium channel 11 along an axial direction, and the medium channel 11 communicates the balloon 3 with the pressure pump connector 7. Targeted expansion and reduction the fracture site is achieved by the balloon through the annular medium channel 11 after contrast agent is filled.

The tube body 5 is further provided with a pressure sensor 6, and the pressure pump connector 7 is provided at a side of the pressure sensor 6. The medium channel 11 is in communication with both the pressure sensor 6 and the pressure pump connector 7.

Figure 4:
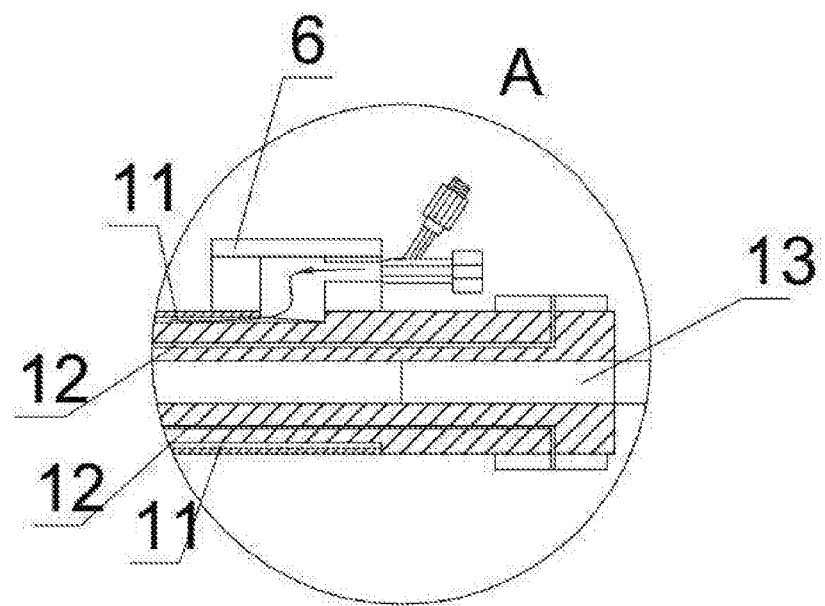
FIG. 4 is an enlarged view of a portion A in FIG. 3.

As shown in FIG. 4, the guider 4 includes a soft spring 16 disposed inside the tube body 5 and a plurality of arc-shaped grooves distributed at an outer wall of the tube body 5. The tube body 5 is provided with a traction rope 12 along an axial direction, and the soft spring 16 is connected to the guide knob 10 through the traction rope 12. The soft spring 16 is bent towards one side under pulling of the traction rope 12, which in turn causes a front end of the tube body to generate torque. Due to the plurality of arc-shaped grooves distributed at the outer wall of the tube body 5, the outer wall of the tube body 5 will be bent under an action of the torque, thereby forming a bendable end.

The guide knob 10 rotates for one revolution, correspondingly, the guider 4 is exactly bent by 90°. A bending angle of the guider 4 is controlled by rotation of the guide knob 10, so as to achieve injection of the cement in different directions.

In order to achieve bending in two directions, two traction ropes 12 are provided symmetrically, and the two traction ropes are connected to two direction control ends of the guide knob 10.

A push rod 9 is further included, and the push rod 9 includes a thin rod 14 and a push rod handle 15 connected to the thin rod 14. The thin rod 14 can be inserted into the cement channel 13. The push rod 9 achieves manual feeding of the cement in the cement channel.

Figure 5:
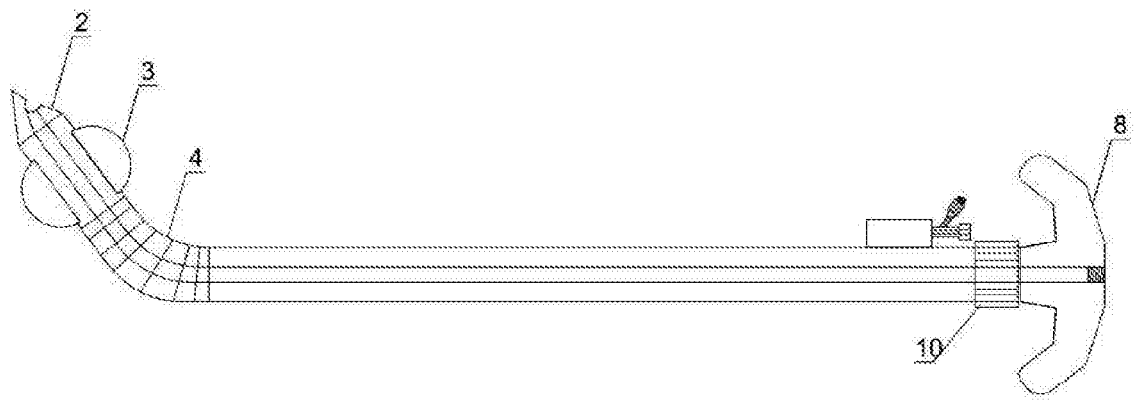
FIG. 5 is a view of an integrated targeted kyphoplasty system of the present disclosure under a using state.
Figure 6:
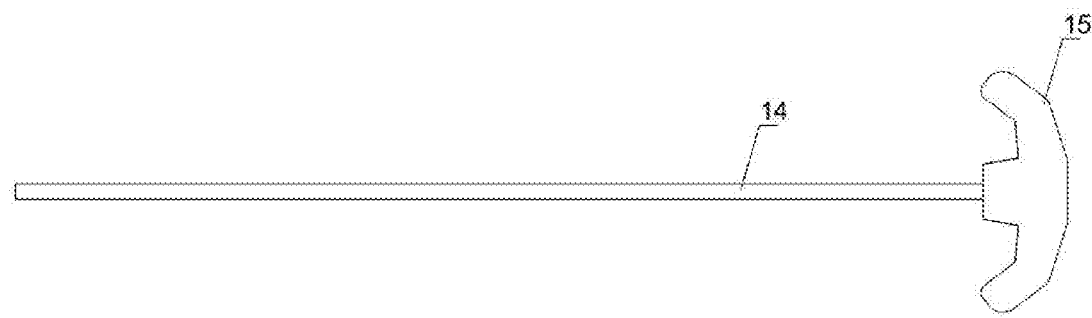
FIG. 6 is a schematic view of a push rod in FIG. 2.

As shown in FIG. 5, a method for operating the integrated targeted kyphoplasty system of the present disclosure is as follows.

1. The piercing head 2 is inserted into the vertebral body in need of surgery, an operation channel is established by controlling the tube body handle 8, and the guide knob 10 is adjusted to cause the guider 4 to be bent when peripheral expansion is required.

2. After the balloon 3 is targetedly placed at a fracture compression site, the balloon is filled with the contrast agent to carry out expansion and reduction of the fracture.

3. The contrast agent in the balloon is then evacuated, and the bone cement is filled. With the bone cement injector being connected to the cement inlet 17, prepared bone cement is injected, and distribution of the bone cement in the vertebral body can be controlled. A flow direction of the bone cement in the vertebral body is controlled according to the guider, so that targeted injection of the bone cement can be accurately achieved, and a problem of leakage of the bone cement is effectively solved due to controllability of infusion of the bone cement.

The integrated targeted kyphoplasty system of the present disclosure has advantages of:

1. improving an efficiency of unilateral piercing, and decreasing duration of surgery;

2. directionally passing through a center-line area of the vertebral body;

3. no damage to an inner side wall of a pedicle;

4. decreasing a number of times of intraoperative radioscopy;

5. decreasing iatrogenic radiation damage;

6. creating an arc-shaped cavity, decreasing destruction of a cancellous bone;

7. increasing inlay connection between the bone cement and the cancellous bone;

8. the bone cement being more evenly distributed, decreasing a probability of re-fracture;

9. a same clinical effect on pain relief;

10. decreasing cost of surgery;

11. decreasing incidence of postoperative pain and subcutaneous hematoma caused by piercing;

12. relieving the patient's pain and discomfort during surgery, and improving the patient's surgical tolerance;

13. targeted expansion and reduction of the fracture, more accurate reduction and better curative effect;

14. targeted injection of the bone cement, with controlled injection and better distribution, decreasing a probability of leakage of the bone cement.

The above embodiments are merely for illustrating implementation of the present disclosure, so that those skilled in the art can implement or use the present disclosure, and the description does not limit the present disclosure. Therefore, the present disclosure will not be limited to the embodiments described herein, and any addition or equivalent replacement made according to the technical features of the present disclosure shall fall within a protection scope of the present disclosure.

What is claimed is:

1. An integrated targeted kyphoplasty system, comprising a piercing head (2), a tube body (5), and a tube body handle (8), wherein the tube body (5) has an end connected to the piercing head (2) and provided with a balloon (3), and the tube body (5) is provided with a guider (4) at an end of the balloon (3);

the tube body (5) has another end connected to the tube body handle (8) and provided with a guide knob (10) for controlling the guider (4) to be bent and a pressure pump connector (7) in communication with the balloon (3); and the piercing head (2) is provided with a cement outlet (1), a cement channel (13) is provided in a center of the tube body (5), the tube body handle (8) is provided with a cement inlet (17), and the cement outlet (1), the cement channel (13) and the cement inlet (17) are in communication with each other.

2. The integrated targeted kyphoplasty system according to claim 1, wherein the cement outlet (1) is provided at a side of the piercing head (2).

3. The integrated targeted kyphoplasty system according to claim 1, wherein an annular groove is provided at the end of the tube body (5), and the balloon (3) is disposed in the annular groove.

4. The integrated targeted kyphoplasty system according to claim 1, wherein the tube body (5) is provided with an annular medium channel (11) along an axial direction, and the medium channel (11) communicates the balloon (3) with the pressure pump connector (7).

5. The integrated targeted kyphoplasty system according to claim 4, wherein the tube body (5) is further provided with a pressure sensor (6), the pressure pump connector (7) is provided at a side of the pressure sensor (6), and the medium channel (11) is in communication with both the pressure sensor (6) and the pressure pump connector (7).

6. The integrated targeted kyphoplasty system according to claim 1, wherein the guider (4) comprises a soft spring (16) disposed inside the tube body (5) and a plurality of arc-shaped grooves distributed at an outer wall of the tube body (5); and the tube body (5) is provided with a traction rope (12) disposed along an axial direction, and the soft spring (16) is connected to the guide knob (10) through the traction rope (12).

7. The integrated targeted kyphoplasty system according to claim 6, wherein two traction ropes (12) are provided symmetrically, and the two traction ropes are connected to two direction control ends of the guide knob (10).

8. The integrated targeted kyphoplasty system according to claim 1, further comprising a push rod (9), wherein the push rod (9) comprises a thin rod (14) and a push rod handle (15) connected to the thin rod (14), and the thin rod (14) is capable of being inserted into the cement channel (13).

\* \* \* \* \*